(12) United States Patent
Shima et al.

(10) Patent No.: US 7,164,476 B2
(45) Date of Patent: Jan. 16, 2007

(54) APPARATUS AND METHOD FOR DETECTING PIPELINE DEFECTS

(75) Inventors: Hiromasa Shima, Cupertino, CA (US); Kenzi Karasaki, El Cerrito, CA (US); David Thomas Iseley, Greer, SC (US); Toru Goebuchi, Saitama (JP); Ko Sano, Saitama (JP); Hiroyuki Iinuma, Saitama (JP)

(73) Assignee: OYO Corporation U.S.A., Pasadena, CA (US)

(*) Notice: Subject to any disclaimer, the term of this patent is extended or adjusted under 35 U.S.C. 154(b) by 542 days.

(21) Appl. No.: 10/258,974

(22) PCT Filed: May 30, 2001

(86) PCT No.: PCT/US01/17390

§ 371 (c)(1),
(2), (4) Date: Oct. 29, 2002

(87) PCT Pub. No.: WO01/92852

PCT Pub. Date: Dec. 6, 2001

(65) Prior Publication Data

US 2004/0021858 A1 Feb. 5, 2004

Related U.S. Application Data

(60) Provisional application No. 60/207,784, filed on May 30, 2000.

(51) Int. Cl.
*G01N 21/88* (2006.01)
*G01N 15/00* (2006.01)

(52) U.S. Cl. .......................... 356/241.1; 250/559.07; 73/865.5; 73/865.8

(58) Field of Classification Search .. 356/241.1–241.6; 250/559.07, 559.22, 559.39, 559.49, 560; 73/82, 865.8, 83, 866.5, 865.5; 324/220, 324/263; 358/100; 348/85; 724/220, 263; 438/85

See application file for complete search history.

(56) References Cited

U.S. PATENT DOCUMENTS 3,739,098 A 6/1973 Latall (Continued)

FOREIGN PATENT DOCUMENTS

DE 35 21 584 A1 1/1986

(Continued)

OTHER PUBLICATIONS

EP01948246 Search Report corresponding case, May 13, 2005, Oyo Corp, USA.

*Primary Examiner*—Layla G. Lauchman
*Assistant Examiner*—Sang H. Nguyen
(74) *Attorney, Agent, or Firm*—Karen B. Tripp

(57) ABSTRACT

An apparatus and method are disclosed for scanning and detecting defects in sewer and similar pipelines that eliminate the need to stop and pan-and-tilt areas of concern. In the method of the invention, a pipeline (15) inspection probe (10) of the apparatus of the invention comprising a CCD camera (14) with fish-eye lens (12) travels through the pipeline (15) on a self-propelled tractor automatically collecting data and transmitting it to a computer to provide a real-time display of the pipeline (15) interior with quasi three-dimensional information for effective and quick data analysis and management. The data includes digitized forward views and unfolded 360 degree laid-flat side-san (22) views of the pipeline (15) interior. Additionally, the digitized data may be stored for further analysis, tabulation, and for use with pipeline infrastructure maintenance software.

23 Claims, 6 Drawing Sheets

U.S. PATENT DOCUMENTS

| | | | |
|---|---|---|---|
| 3,832,724 A * | 8/1974 | Duval | 396/19 |
| 4,249,810 A * | 2/1981 | O'Connor et al. | 396/19 |
| 4,317,632 A * | 3/1982 | Orphan et al. | 356/241.1 |
| 4,355,904 A * | 10/1982 | Balasubramanian | 356/608 |
| 4,725,883 A * | 2/1988 | Clark et al. | 348/84 |
| 4,752,127 A * | 6/1988 | Zafred | 356/241.1 |
| 4,963,018 A * | 10/1990 | West | 356/3.05 |
| 4,967,092 A * | 10/1990 | Fraignier et al. | 250/559.07 |
| 4,974,168 A * | 11/1990 | Marx | 702/187 |
| 5,099,115 A * | 3/1992 | Cruickshank | 250/236 |
| 5,195,392 A * | 3/1993 | Moore et al. | 73/866.5 |
| 5,717,455 A * | 2/1998 | Kamewada | 348/85 |
| 5,895,927 A * | 4/1999 | Brown | 250/559.19 |
| 6,243,657 B1 * | 6/2001 | Tuck et al. | 702/150 |

FOREIGN PATENT DOCUMENTS

| | | |
|---|---|---|
| EP | 0 831 299 A | 1/1998 |
| EP | 0 846 840 A | 6/1998 |
| EP | 1 022 553 A | 7/2000 |

* cited by examiner

APPARATUS AND METHOD FOR DETECTING PIPELINE DEFECTS

RELATED APPLICATION

This application claims priority to U.S. Provisional Patent Application No. 60/207,784, filed May 30, 2000.

BACKGROUND OF THE INVENTION

1. Field of the Invention

This invention relates to apparatuses and methods for inspecting the interior of conduits and pipes, particularly pipelines, such as sewers, air ventilation ducts, or liquid or gas transport pipelines, and locating defects such as corrosion, joint separations, cracks, depressions, or crushes in same, as well as roots, debris, blockages, and the like. More specifically, this invention relates to viewing devices and methods for movably scanning the interior of pipes or pipelines and to the collection of data for analysis and interpretation of the results of such scanning to evaluate the condition of the pipelines and the location of any defects in the pipelines.

2. Description of Relevant Art

As used herein, the term "pipeline" or "pipelines" shall be understood to include conduits, pipes, and ducts as well as pipelines and other such lines for transporting storm or sanitary sewage, air, liquids, gases or slurries. Known systems for inspecting pipelines typically comprise a television camera or a video camera mounted on a self-propelled electric tractor or on a sled pushed by a semi-rigid cable along the pipe from an open end of the pipe. Lights are attached to illuminate the pipeline interior. Both the lights and the camera are powered by the cable. An image of the pipeline is captured by the camera and recorded by a VCR (video cassette recorder) for viewing. The standard mode of operation employs pan, tilt and zoom capabilities by the camera. A forward looking view down the center of the pipeline is typically displayed and recorded, unless the operator stops to take a closer look—to pan, tilt and zoom—at a particular area of the pipeline. The taking of a closer look is dependent on the operator's subjective judgment during the inspection. If the operator, for whatever reason, does not visually identify an area of potential interest or concern (cracks, roots, etc.) in the forward looking view, the opportunity to stop, pan, and tilt to get more detailed information is lost. If a subsequent view of the video tape alerts another viewer to a potential problem area, detailed information can only be acquired by reinspecting the pipeline.

Common problems with known commercial systems have included inability to accurately gauge the location of a detected defect, insufficient lighting to identify a defect, distortion of image, inadvertent missing of defects, uneven quality and subjective defect classification, and requirement for burdensome review of volumes of video tapes after the inspection in an effort to decipher the video tapes and to distinguish defects from shadows. Most typically, use of known commercial systems can result in oversight of critical cracks and other defects in the pipeline.

Canadian patent application no. 2,216,800 of Core Corp. generally discloses or suggests a device using a beam of light reflected off of a rotating mirror said to provide a 360 degree round image of a pipeline. However, this device does not appear to include a digital forward view of the pipeline.

There continues to be a need for improved methods and apparatuses for fast, accurate and economical inspection of pipelines and evaluation of data associated with same.

SUMMARY OF THE INVENTION

An apparatus and method is disclosed for inspecting or scanning the interior of a sewer line (or other similar pipeline) that eliminates the need for and consequent delay associated with stopping for pan and tilt closer inspection and that provides objective inspection. Moreover, an apparatus and method is disclosed that provides a real-time digitized and synchronous forward view and a 360 degree peripheral or side-scan view of a pipeline. The continuous digitized real time images may be saved for later evaluation.

The apparatus of the invention comprises a probe with an optical viewer or visual sensor, such as for example a video or CCD (charged coupled device) camera (or preferably a 3CCD camera, and as used herein with respect to the invention, the terms optical viewer or visual sensor or camera shall be understood to include without limitation any and all of these various kinds unless specifically indicated to the contrary) with a fish-eye lens (or other lens capable of performing a similar function of viewing in wide angles), a mover for carrying the probe into and out of the pipeline, such as for example a self-propelled tractor, a light or light source, such as for example at least one ring of LED lights, a power supply for the light source and for the camera, a distance measurer, an inclinometer, gyroscope and/or other location or direction detector, data processing software and a computer for running said software and for collecting, digitizing, and manipulating the data, displaying the results, and saving the data for further analysis, further evaluation, or for use with pipeline infrastructure maintenance software as desired.

The data processing software of the apparatus of the invention should have the capability of performing the data processing steps in the method of the invention, and the computer of the apparatus should have sufficient memory and processing power to store and manipulate the data collected. For most applications contemplated, the computer (including computer display) portion the light, the optical sensor, the distance measurer, and the location, direction, or orientation detector or detectors will be sent into the pipeline for data collection or acquisition. Connection between the probe and the computer is preferably made through appropriate cabling for transport of data to the computer, although it is anticipated that wireless communication may be possible in some applications. Connection is also made between the probe and a power source.

In the method of the invention, a probe comprising, or having associated therewith, a light or light source, a visual or optical sensor or viewer (such as for example a video or CCD, or preferably a 3CCD camera, and as used herein with respect to the invention, the terms optical viewer or visual sensor or camera shall be understood to include without limitation any and all of these various kinds unless specifically indicated to the contrary) having the ability to view wide angles, preferably about 360 degrees, such as with a fish-eye lens or wide-angle lens, a distance measurer, and a direction, orientation or other location detector, is obtained and transported into and moved through at least a portion of a pipeline whose interior is to be inspected. The probe must be sufficiently small to fit into and to be moved through the pipeline to be inspected without damaging the pipeline. Preferably, the probe will also be comprised of materials that will not interfere with the operation of the pipeline. The probe is connected to, or otherwise in communication with, a computer (which need not be on the probe itself and preferably is located where at least the computer display can be viewed by persons on the surface and not themselves in the pipeline.)

As the probe is moved through the pipeline, the optical sensor or visual viewer scans (in about 360 degree views) the pipeline wall and at specified intervals takes forward (or frontal) views and side-scan views (or forward views that will be digitized and processed to make unfolded side-scan views) which are sent as output to the computer. At the same time or substantially the same time as the views are being taken by the optical sensor or visual viewer, the direction and location detector or detectors is providing output to the computer concerning location of the probe at the time of the scan, and such information preferably includes at least the angle of inclination and axial rotation of the probe. Also at the same or substantially the same time, the distance measurer is providing information to the computer about the distance that the probe is in the pipeline. Preferably for sewer pipes, typically less than about eight to about twenty-seven inches in diameter, the side-scan views (or forward views that will be digitized and processed to make unfolded side-scan views) are taken about every one or two millimeters, and the forward views are taken about every 100 millimeters, of distance into the pipeline that the probe is traveling as it passes through the pipeline. Many other intervals may alternatively be used, depending on the purpose or use (i.e., the type of liquids or gases the pipe may carry) may influence the pipeline detail desired. Scans as frequently as about every 0.1 millimeter are generally achievable.

The scans or taking of the views is preferably automatic and continuous, at whatever intervals selected, and thus full coverage of the interior surface of the pipeline is obtained (without need for subjective decisions concerning any particular area of the pipeline). The probe is not stopped while the views are taken and the views are transported as output to the computer for processing and preferably real-time display at the pipeline surface. Preferably, an operator at the surface of the pipeline monitors the real-time digitized display for comparison to the video picture from the optical sensor or video camera, also being displayed real-time. This comparison is preferably done to ensure quality performance of the probe and the data processing. Typically and preferably, all or substantially all forward views taken are displayed, but fewer forward views are recorded and saved. (That is, many multiple forward scans that are digitized and processed to make unfolded side-scan views are typically or preferably saved less frequently whereas the portion comprising the multiple side-scan lines in every forward view frame is preferably saved.) Although not necessary for the present invention, the actual picture from the optical sensor or video camera may also be recorded and saved if desired.

With equipment commonly available today, the views taken by a video camera are in NTSC (National Television System or Standards Committee) video output format. This output goes into a frame capture board for conversion from analog to digital data. (In the future, the output may instead be originally taken and transmitted in digital form). Pixel manipulation software then manipulates the digital data to obtain unfolded side-scan images of the pipeline interior. The unfolded side-scan images of the pipeline are created by identifying the pixels that fall on a pre-specified sampling circle on each frame captured by a frame capture board and then correcting the data with the rotation angle data from the inclinometer. For faster scanning, more than one sampling circle may be used (that is, the sampling circles may be used in multiples). Inclinometer data is used to locate the direction of the pipeline bottom (or lowest point with respect to gravity) for "cutting" the side-scan image to "unfold" it (i.e., unscroll it or cause it to be laid-flat) for real-time visualization of the laid-flat pipe image. The side-scan image could be cut and unfolded at other points of the pipeline than the bottom.

Further with respect to the preferred method of the invention, the digitized forward view and the digitized unfolded side-scan view may be viewed simultaneously on the computer display in real-time as the probe passes through the pipeline. Still further, the digitized views may preferably be compared in real-time to the video picture being transmitted (also in real-time) from for use with pipeline infrastructure maintenance software.

DESCRIPTION OF THE PREFERRED EMBODIMENT OF THE INVENTION

An apparatus and method are disclosed for scanning the interior of a conduit, pipe or pipeline to determine defects in the interior of such pipeline. Such "defects" as the term is used herein is understood to include joint separations, corrosion, cracks, depressions, or crushes and the like in the pipeline, and even obstructions or projections (such as roots or debris) and the like in or into the interior of the pipeline, and also any other visible feature, characteristic, or condition of the pipeline that may be of concern or interest for inspection or determination. The pipelines suitable for inspection with the apparatus and method of the invention are preferably positioned substantially horizontally or at least off of vertical. The advantages of the invention may be especially appreciated with pipelines that are buried underground and with pipelines that transport liquids, gases, or slurries, such as sewer lines. Further, the advantages of the invention may be especially appreciated for inspection of pipelines that are too small in diameter or too hazardous to be entered by a person for inspection.

The apparatus and method provide a view of the interior wall of the pipeline from a scan view of the pipeline interior wall. The side or side-scan view is an "unfolded image"—a two-dimensional representation of a three-dimensional pipe which is equivalent to cutting the pipe and unfolding it and laying it out flat. This laid-flat or side-scan view can be displayed and digitally recorded simultaneously with the forward view, which is also displayed and digitally recorded.

Figure 3:
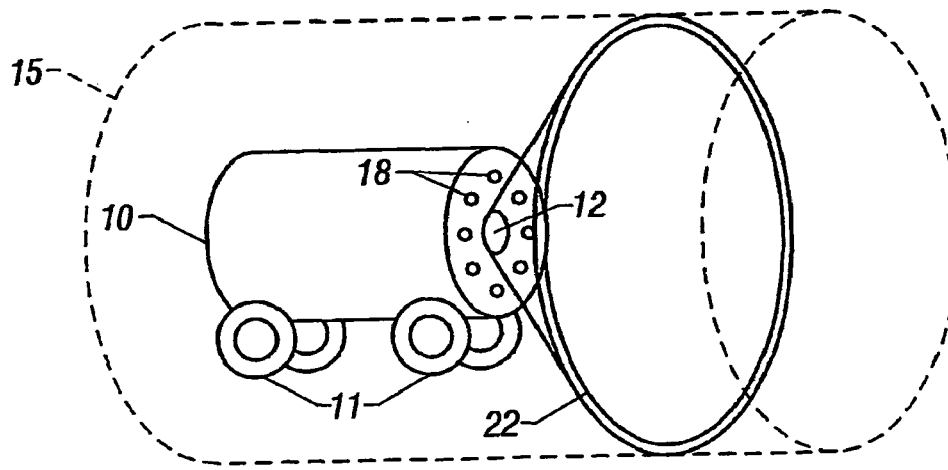
FIG. 3 is a schematic side view of the pipeline inspection probe portion of the apparatus of the invention on a wheel type mover in a pipeline (transparent for illustration) showing the location of the wide angle or fish-eye lens and the accompanying 360 degree radius of the sampling circle automatically taken by the apparatus.

This side-scan view is made from a digitized 360 degree forward view taken with a wide-angle or fish-eye lens (or other lens or optical sensor or viewer capable of viewing wide angles) as depicted in FIG. 3, as will be further discussed below. As used herein, reference to taking a side-scan view shall be understood to refer to scanning the pipeline and taking visual information or data that will ultimately, after processing, result in an unfolded side-scan image of the pipeline wall which may be displayed and digitally recorded. Forward views that are processed to make side-scan images are displayed and saved as forward views but preferably saved at a less frequent interval than side-scan lines.

The apparatus of the invention generally comprises two parts—a field data acquisition or collection part, also often called the pipeline inspection probe, and a data processing part, which is often referred to as the control center or control unit comprising at least one computer or data processor and software. At least the pipeline inspection probe portion of the apparatus is placed inside the pipeline. The control center portion is preferably outside of the pipeline and most preferably on the surface above or near the pipeline.

Figure 1:
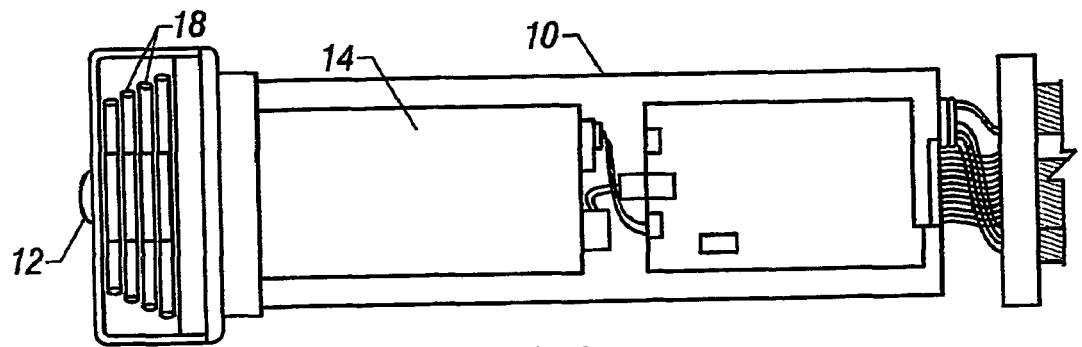
FIG. 1 is a cutaway schematic view of the pipeline inspection probe of the apparatus of the invention.

An example of a pipeline inspection probe of the apparatus of the invention may be depicted as shown in the schematic of FIG. 1, which illustrates a cutaway view. This part of the apparatus of the invention comprises a probe or probe body 10, visual viewer or optical sensor 14, which is preferably a video or CCD camera or more preferably a 3CCD camera, and associated lens 12, which is preferably a fish-eye lens. The fish-eye lens 12 in or associated with the camera 14 enables the viewing of the forward views on sampling circle(s) on the pipeline interior preferably in wide angle (most preferably 360 degree) radius scans as shown in FIG. 3 as scans 22. Other lens that could accomplish this result could alternatively be used.

The apparatus of the invention further comprises a light or light source 18, which is preferably at least one and most preferably multiple LED lights which are preferably evenly spaced one with respect to the other, and an inclinometer (not shown), preferably a gyroscope or gyroscope sensor (not shown), and/or other device or devices (not shown) for providing information concerning the posture of the probe and therefore the location and direction of the pipeline.

The camera 14, lens 12, and lights 18 (and other components comprising the probe 10 or on or attached to said probe 10 such that said camera 14 and lens 12 may view the pipeline interior without obstruction from any other components of the probe and said lights 18 may illumine the interior of the pipeline so that the views taken by the camera 14 may be clearly seen.

Light is essential for high quality optical pipeline inspection. Light sources such as LED lights that provide a brilliant, stable, long-lasting light are preferred for use in the present invention. Halogen bulbs readily available today tend to be too unstable for preferred use in the present invention. That is, the luminosity provided by halogen bulbs changes over time, and the luminosity provided by halogen bulbs is not-uniform, i.e., the luminosity changes in direction from source. Moreover, halogen bulbs generate significant heat. Heat generated by the light source can cause large errors with optical video sensors like a CCD sensor and gyro sensors because such sensors have a temperature dependent drift nature. LED lights do not generate a significant, if any, amount of heat. LED lights are also relatively long lasting when compared with halogen bulbs. The longer lasting the light source the better for the invention because bulb replacement can cause down time and field delays.

As shown in FIG. 1, the LED light source 18 of probe 10 preferably has a ring shape. In one example embodiment, about 20 small but high luminosity LED lights are placed along the ring at a constant interval. In another example embodiment, more than one ring is used, as shown in FIG. 1, which has 4 rings of about 24 LED lights. The exact number of lights needed will depend at least in part on the size of the probe and the pipeline. These equally distributed LEDs realize a uniform luminosity in any direction from the optical sensor. This luminosity may also be easily adjusted by changing the voltage applied, a further advantage of this invention.

Figure 2:
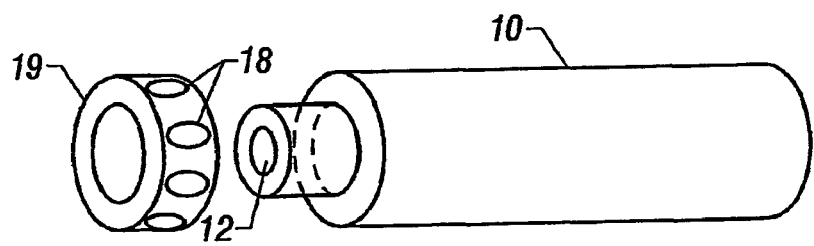
FIG. 2 is a schematic side view of the pipeline inspection probe of the apparatus of the invention with the light source separated therefrom for illustration.

FIG. 2 shows a schematic side view of probe 10 with the light source 18 separated or removed from the probe 10 to better illustrate detail of the light source 18. As shown in FIG. 2, the light source 18 is preferably mechanically designed in such a way that a field operator can easily exchange the light source module 19 without reassembling the main part of the pipeline inspection probe 10. Thus, for example, if one of the LEDs in or on the ring dies or ceases to emit light, the field operator can exchange a "plug-in" light source module. The term "plug-in" as used herein is meant to be a generic term for any number of mechanical embodiments or operations that allow for removal and replacement of the light source module 19 onto the main body of probe 10. This exchange feature of the light source of the system of this invention is particularly advantageous with pipeline inspection probes that have been water-proofed, such as by filling with nitrogen gas. The light source may be replaced without disturbing the main body of the probe or requiring its reassembly, and thus without interfering with any water proofing of the The apparatus of this invention also preferably has an improved gyroscope sensor associated with the probe 10 or attached to the probe 10 or the camera 14 for identifying the exact location and direction of the camera 14 in the pipeline which in turn allows for identity of the exact location of a pipeline defect seen with the camera. More specifically, the system of this invention and particularly the data collection component of the apparatus of the invention preferably has accurate gyro sensors that measure pipeline deflection that is associated with the location data.

Deflection of a pipeline may be measured in various ways; the most common three ways are with an accelerometer, with a magnetometer, or with a gyro sensor. Any of these could be used for the present invention, subject to the following limitations. The accelerometer depends on gravitational field so that only vertical deflection can be measured. The magnetometer depends on the earth's magnetic field and so is affected by nearby subsurface and/or surface metal structures and consequently is useless in metal pipes. The gyro sensor was originally developed for fast moving objects such as airplanes, missiles, etc., and is thought to provide accurate data only when it moves relatively fast. However, for use with the present invention, we have discovered a way to eliminate noise from gyro data stored with time information that enhances the use of gyro sensors, even at slower speeds more often preferred for pipeline inspection.

The output of the gyro sensor is known to be angular velocity. To generate the angle of pipe, the angular velocity must be integrated with time, and to generate deflection (trace) of pipeline, another integration of the angle with distance is needed. When an object moves slowly like a pipeline inspection probe, the output of angular velocity is very small and heavily polluted by noise. When this data is integrated to generate deflection, the noise is also integrated and this enhanced noise can make the generated deflection meaningless, at least as seen in the prior art.

However, we have discovered that when the main component of the noise depends on the nature of the sensor, and when the conditions of measurement such as temperature and speed of an object are fairly constant, then the noise is also fairly constant. The following two way procedure may then be used to eliminate the noise from the gyro data stored with time information.

In this compensation method for gyroscope data, gyro data is measured two ways—going forward in the pipeline and coming back through the pipeline. If the data has no noise, the generated final direction of the probe must be the same as the direction when it was at its starting point. If a difference is observed, then this difference in angle, called Theta-error, can be considered the integrated amount of noise. Noise generation speed, Theta-error/T, is calculated by dividing the Theta-error by the total time of measurement (T). Measured gyro data is recalled with time information, Theta (t), where "t" is the time from beginning of the measurement. The $$Theta\text{-}c(t)=Theta(t)-Theta\text{-}error/T*t.$$

The pipeline trace (deflection) is then calculated by integrating the compensated angle with distance.

For example, a computer simulated this correction or compensation for gyroscopic data from a gyroscope sensor running from the left to right at the speed of about 20 mm/second. After the sensor reached the distance of about 1000 mm, the sensor returned to the starting point. The total time of the measurement was 100 seconds (=1000 mm*2/20). True inclination was set at 10 degrees from 220 mm to 300 mm distance, at 5 degrees from 320 mm to 400 mm, at −5 degrees from 620 mm to 700 mm and at −10 degrees from 720 mm to 800 mm. Supposing, for example, that Theta-error after a round trip was 1 degree, then Theta-error/T was 0.01 degree/second and Theta-c(t) was calculated by Theta-c(t)=Theta(t)−0.01*t for this case. The computer simulated data was then compared with real data and satisfactory comparison was seen.

The apparatus of the invention also preferably has an automated camera vibration correction which uses the gyroscope data for a hardware based correction and has a software based correction which keeps the center of the pipeline in the same position on the output or data display.

Referring to FIG. 3, the probe 10 may further comprise, be attached to, fitted with, or otherwise associated with, a mover for moving the probe through the pipeline 15. A preferred mover for the probe 10 is a self-propelled tractor on which the probe rests and is attached. Other suitable movers include for example without limitation wheels 11 fitted directly onto or part of the probe. Alternatively, the mover could be a sled or slide for sliding or pulling or pushing the probe through the pipeline. In still another embodiment, the mover could be a cable for holding and pushing or pulling the probe. The mover may be any means that effects such movement of the probe through the pipeline, which movement should preferably be smooth, steady, consistent and easily controlled. The mover should also preferably provide a stable support for holding the probe relatively steady during movement in and through the pipeline. Further the mover should also preferably be comprised of material that will not damage or interfere with the utility of the pipeline, and should preferably operate in a manner, i.e., provide movement to the probe through the pipeline, that will not damage or interfere with the utility of the pipeline. Further, the probe and the mover should preferably be of sufficiently small size to have utility in a broad spectrum of size ranges of pipe and to preferably be able to turn pipeline corners.

Alternative embodiments of this invention are foreseen where the pipeline has incorporated within it, permanently or semi-permanently installed, data acquisition elements of this invention such that a mover is not needed to move a probe and a mobile probe itself is not used to contain The apparatus of the present invention also preferably comprises or has associated therewith a distance meter or measurer for measuring or determining the distance of the probe in the pipeline when the various views of the pipeline are taken. Such distance is needed to determine where the probe and camera are and hence where in the pipeline any defects that are detected are located. Such distance measurer may be partially on the probe and partially at the exterior surface of the pipeline but wherever located should preferably be able to provide distance information in real-time with the scan of the pipeline interior. Distance measurement is typically made for or associated with the side-scan image (or the forward view that will be processed to make the unfolded side-scan image) by the camera. However, the particular method or equipment used to determine such distance is not critical so long as the determination is accurate.

One example of a distance measurer suitable for use in the apparatus of the invention is a winch comprising cable (not shown). The length of the cable will be determined by the need—the length of the pipeline to be evaluated—and availability. One example length that may be typical is 1000 feet of cable but wide variation in the cable length is possible and expected. Such winch and cable are used for running cable into the pipeline with the probe 10 for measuring distance of the probe 10 in the pipeline.

A winch and cable may also be used for providing communication with the probe 10 for controlling direction of the probe 10, for providing energy to the probe 10, etc., and for receiving information and data back from the probe 10 and the probe 10 components such as sensors and camera 14 to the control center (not shown). A control center (or control unit) may be used or positioned on the surface or elsewhere outside the pipe in the field to provide a power supply to the probe and to control the lights and the mover for the probe and also to receive and store data received back from the probe 10 or its various or associated components. Alternative methods may be used to control and/or provide energy to the probe and/or to receive data, including laser and infrared technology. Most preferably, fiber optics or fiber optic cable is used to communicate with the camera 14 and particularly the fish-eye lens 12.

In the method of the invention, a pipeline inspection probe of the apparatus of the invention, or a data collection apparatus with similar capabilities as that of the apparatus of the invention, preferably automatically takes a forward view (or a forward view that will be processed to make an unfolded side-scan view) of the pipeline interior as the probe (with camera) moves along the pipeline. (In an alternative embodiment, the probe preferably automatically takes digitized forward and side-scan views of the pipeline interior wall as the probe (with camera) moves along the pipeline.) The exact periodic distance for the scans will depend in part on the However, a practical and typical (but not meant to be limiting) example distance for use of the invention in typical sewage pipelines is every ten centimeters (or one hundred millimeters) for the forward view and every one or two millimeters for the side-scan view. The data collection apparatus also takes a reading of the angle of inclination and axial rotation of the probe, preferably with each view or at least preferably with each side-scan view.

Figure 5:
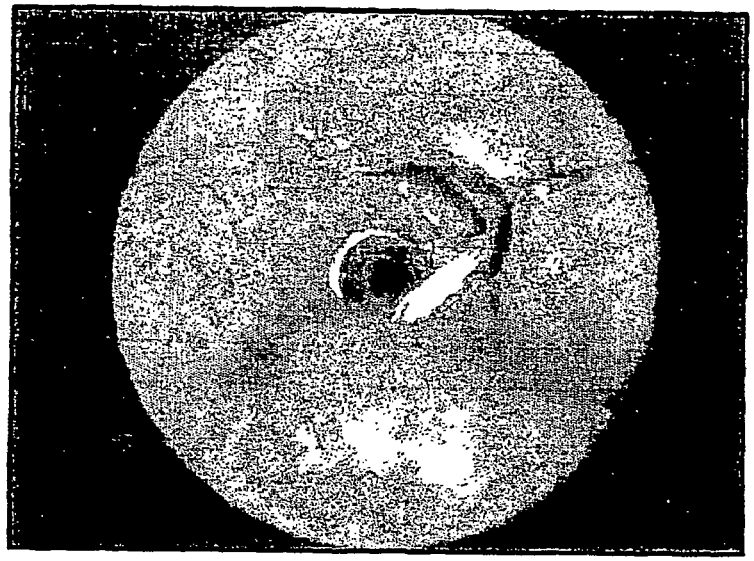
FIG. 5 is a photograph of a forward image of the interior of a pipeline obtained using the invention.
Figure 6:
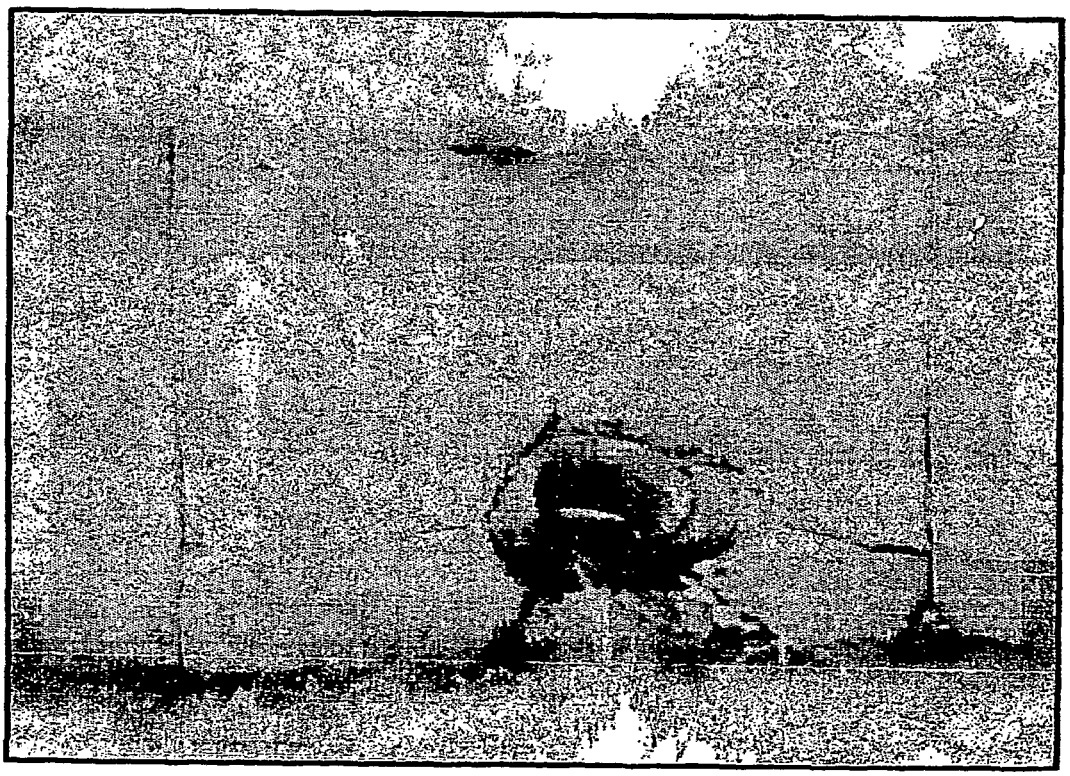
FIG. 6 is a photograph of an unfolded side-scan laid-out flat image of the interior of a pipeline obtained using the invention.

The data processing part of the apparatus of the invention uses this data to provide the field operator with a quasi-three dimensional understanding of the internal view of the pipeline as well as of the deflection of the pipeline (both vertical and horizontal deflection). A preferred computer monitor display preferably provides the operator simultaneously with a forward-looking view in the pipeline, an unfolded side-scan of the pipeline interior wall, and a compass or gyroscope display of deflection as well as a data quality indicator. FIG. 5 shows an example forward-looking view that may be seen on the display and FIG. 6 provides an unfolded side-scan image of a pipe that may be seen on the display. The control center may also include a real time video, CD, DVD, or hard disk recording of the pipeline scan which may be displayed preferably on another screen, such as a video or television screen, for comparison with the display of the digitized forward-looking view.

In general terms, the display layout for the real-time digitized data collection of this invention can be understood by considering a cylindrical coordinate system having an x-axis for the direction of the pipeline, a t-axis for the azimuth direction along the pipeline wall, and an r-axis for the direction perpendicular to the pipeline wall. A 360 degree unfolded side-scan view provides a two-dimensional image of the x-t plane and a forward-looking view provides a two-dimensional image of the t-r plane. The forward-looking view gives the image where the data collection system is going to from now on, and the side-scan view gives the image where the data collection system has passed through already. The deflection of pipeline is indicated with both numbers (vertical inclination and horizontal meander) and a directional arrow (or other directional indicator) in a three-dimensional system. Data quality indicators, such as roll angle of the data collection system, deviation from suitable speed, etc., allow the operator to maintain the data collection (by the pipeline inspection probe) under suitable conditions or within preferred limits.

Figure 4A:
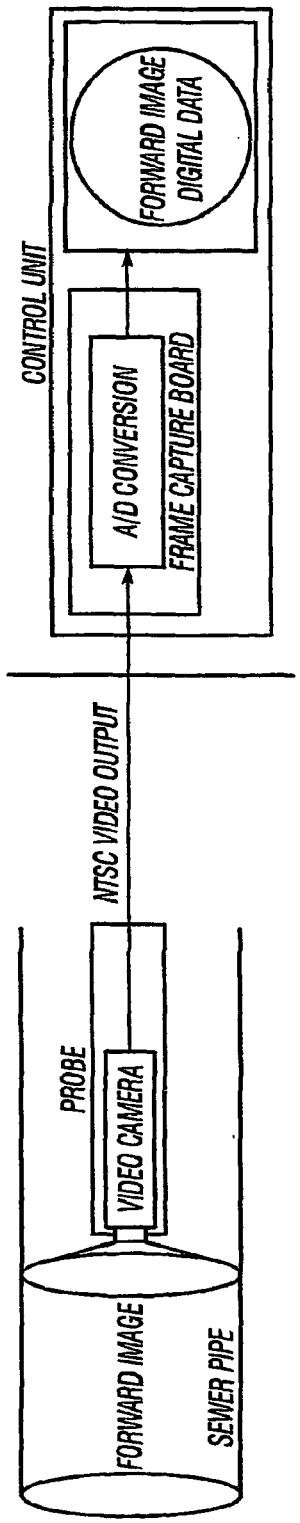
FIGS. 4a–g provide a flowchart and schematic of steps for unfolding a side-scan image of a pipeline interior taken using the apparatus of the invention according to the method of the invention.
Figure 4C:
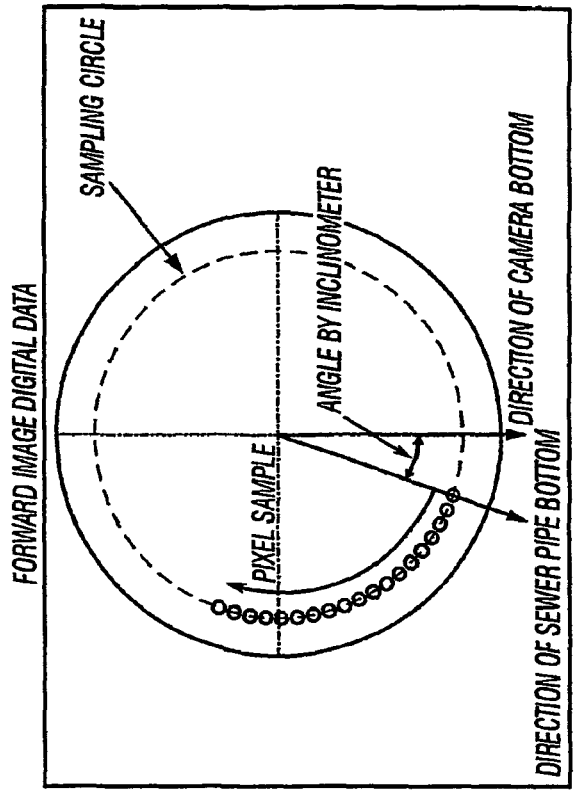
Figure 4B:
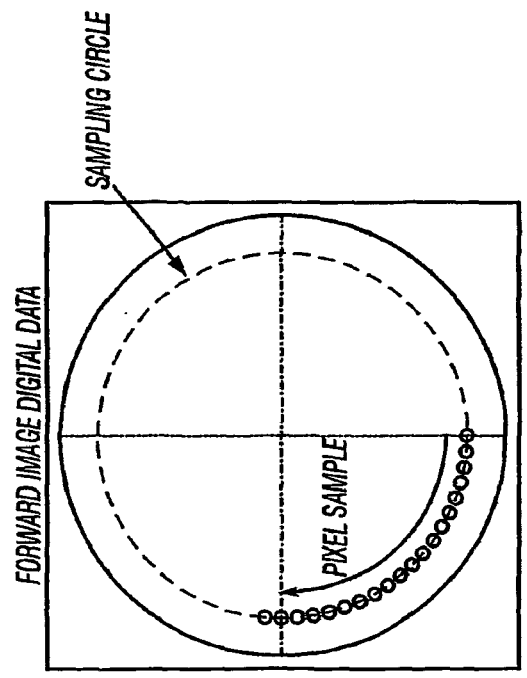

All of the raw data collected by the pipeline inspection probe or the field data collection part of the apparatus of the invention is fed into a computer programmed to digitize the data and outputs from the field data collection part of the apparatus—at least the forward-looking view, the distance and the direction of the field data part of the apparatus when taking the views—using data processing software, including the software outlined in the flowchart and schematics at Figures FIGS. 4a–g outline the steps involved in analyzing and interpreting the pipeline inspection probe data output to obtain a side-scan unfolded image of the pipeline interior at any particular point along the pipeline. Referring to FIG. 4a, NTSC video output data from a forward image scan with the field data acquisition part (the pipeline inspection probe) of the apparatus of the invention according to the method of the invention is transmitted to the data analysis and interpretation part (the control center) of the apparatus of the invention. In the control center, the analog data is converted to digital data on a frame capture board. Pixels that fall on a pre-specified circle—the sampling circle—in each frame are identified, as schematically shown in FIG. 4b. The sampling circle is placed such that it is concentric to the center axis of the pipe—the point at the far end of the pipe where the image seems to converge to a point. Thus, the sampling circle is located on the inner circumference of the pipe image. The diameter of the sampling circle may be changed to adjust the view angle. The larger the diameter, the wider the view angle.

Using the inclinometer data, the bottom of the pipe is determined, as shown in FIG. 4c. The side-scan image could be cut and unfolded at other points of the pipeline than the bottom. The bottom, however, is the location most often containing debris and thus is the location that may consequently contain less helpful data and thus is the point thought most suitable for cutting for the unfolding of the image.

Figure 4D:
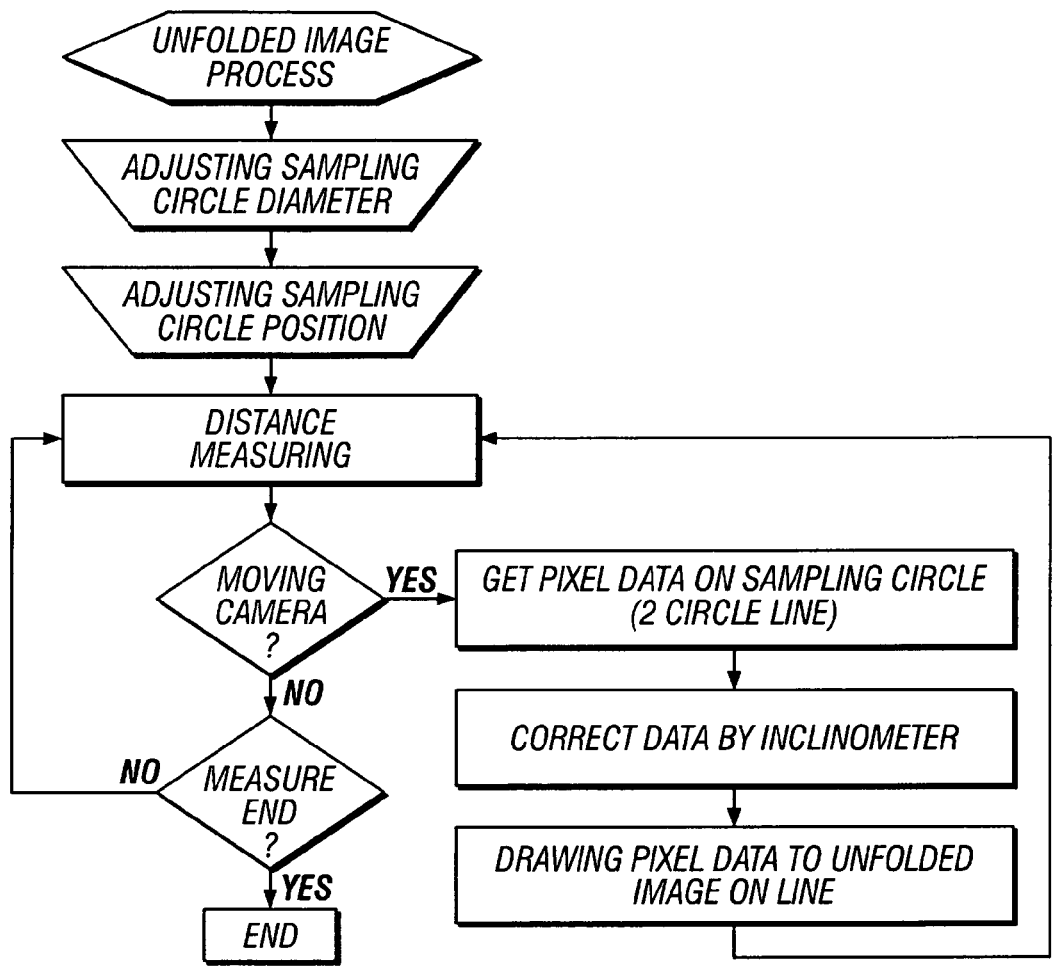
Figure 4E:
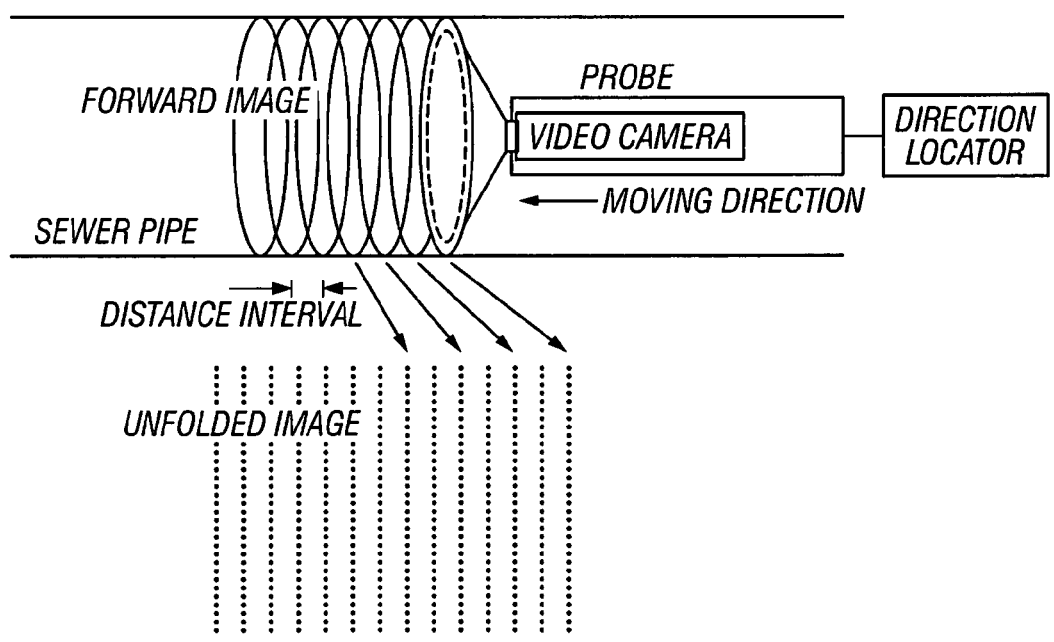
Figure 4F:
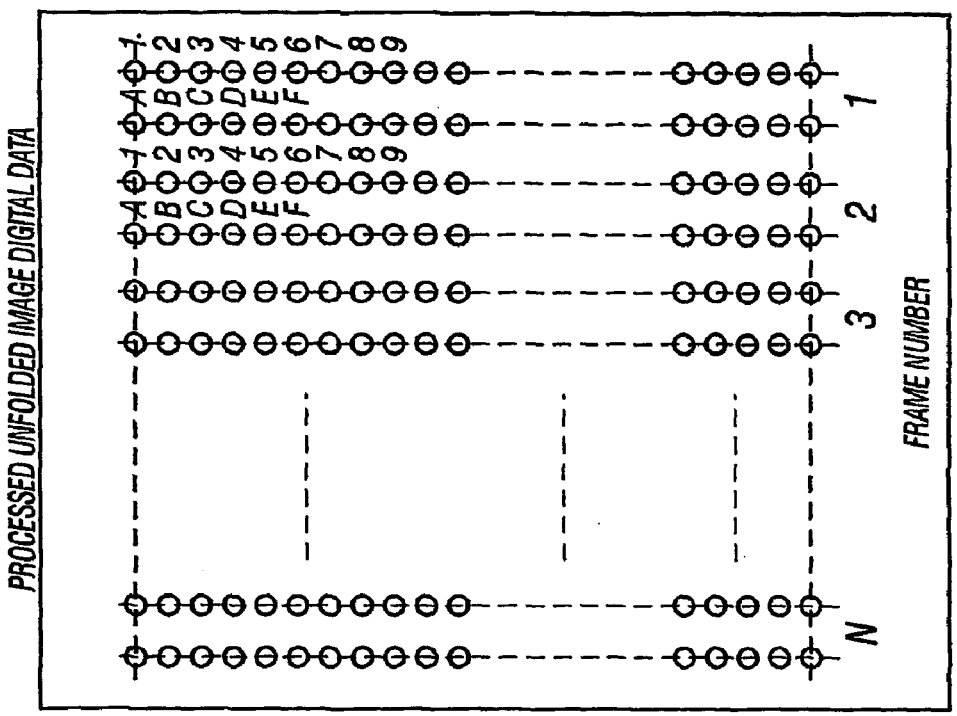
Figure 4F:
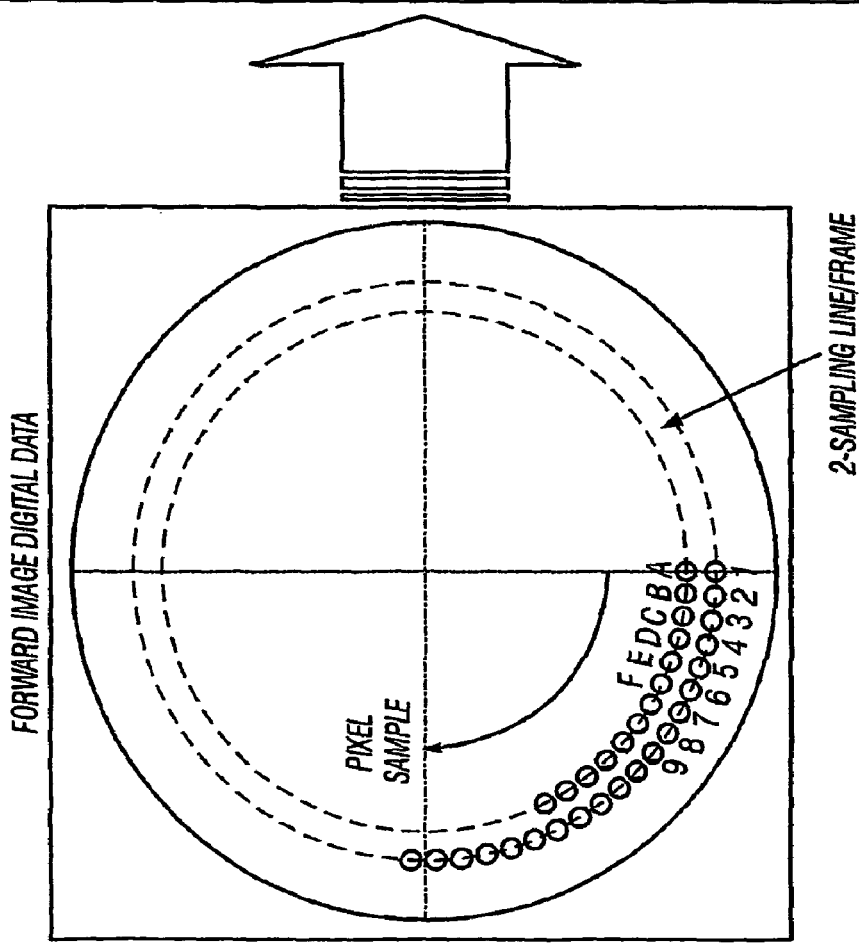
Figure 4G:
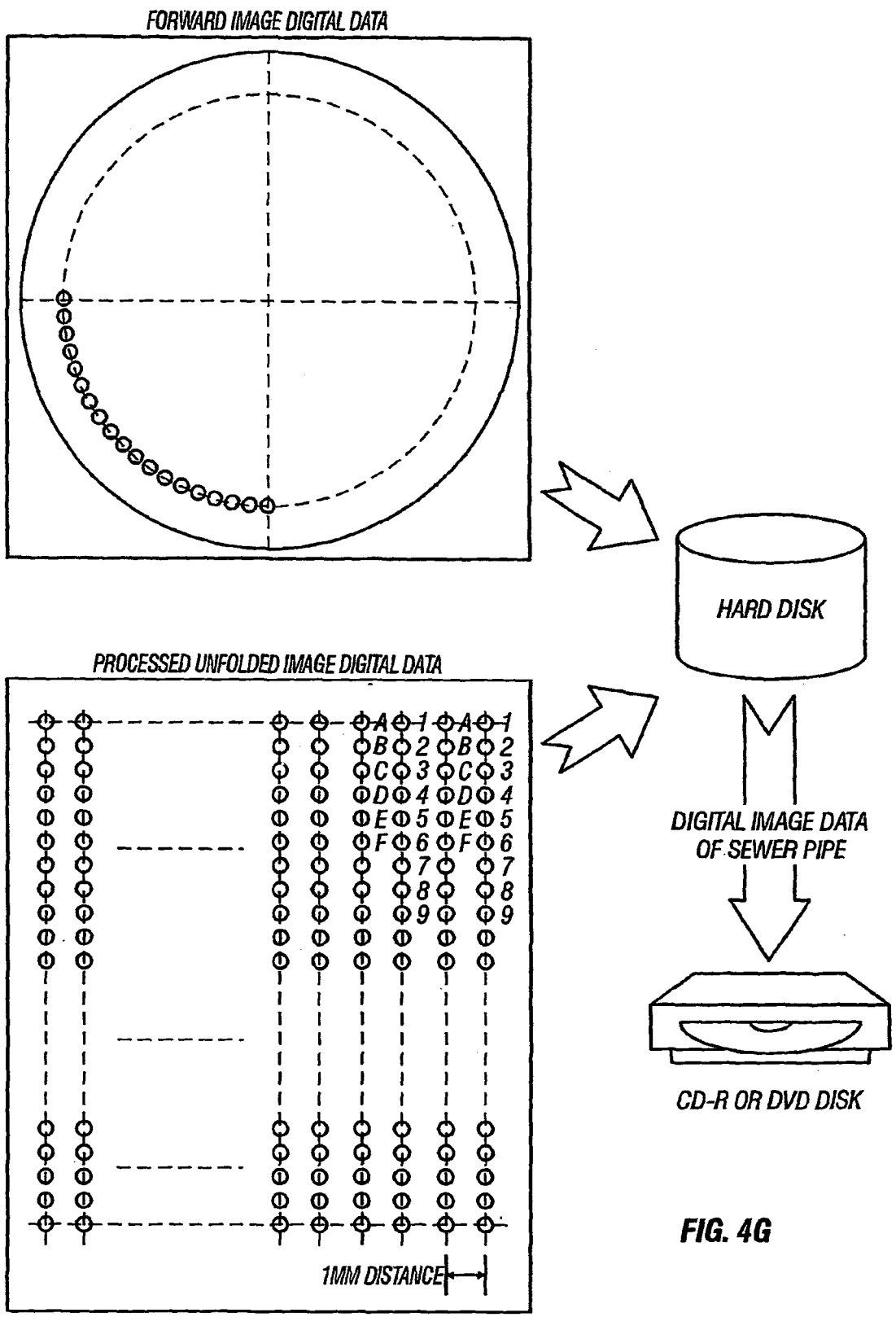

NTSC video output data of a forward view that will be processed as an unfolded side-scan view taken with the probe is transmitted to the control unit and processed as depicted in the flowchart at FIG. 4d and in the schematic at FIG. 4e, showing a processed unfolded side-scan image. Typically, one sampling circle is used. For faster scanning, pixels can be obtained on preferably two or more sampling circles and drawn on the unfolded image—two or more lines for every frame with the video or CCD camera moving. FIG. 4f schematically depicts the procedure for rearranging the pixels that are on the scan-ring line so that they line up in a straight line with the bottom most two pixels at the opposing ends, to create an "un-folded" side-scan image. Finally, the two images—the forward view and the unfolded side-scan view—are shown on the display in the control center at FIG. 4g. "Zooming" in on the views preferably should be available from the display. Also as illustrated in FIG. 4g, this digitized image data may be saved for later use, manipulation, or processing.

Other software needed for the data processing of the output from the pipeline inspection probe of the invention is commonly available and known to those skilled in the art, such as software for converting analog data to digital data and software for manipulating pixels on a frame capture board, including software to obtain a forward view of the pipeline. Preferably, the preferably, all such collected digital data may be saved and stored on electrical media such as CD, DVD, hard disk, or other storage media or method desired.

The data processing software selected for use in or with the invention preferably should enable a quick search of specific data sets, replay of the data, and application of processing such as filtering. The software also preferably should allow an interpreter to put interpretation or comments on the display or image, and/or to add interpretive diagrams and statistics to the original data set.

The data set format provided by use of one embodiment of the apparatus and method of the invention is attached as an Appendix. These data sets would allow one skilled in the art to use and manipulate the digitized data output from the invention in any manner desired, such as for further evaluation, tabulation, and use with pipeline infrastructure maintenance software.

The foregoing description of the invention is intended to be a description of preferred embodiments. Various changes in the details of the described method and apparatus can be made without departing from the intended scope of this invention as defined by the appended claims.

What is claimed is:

1. A method for detecting defects or damage in the interior wall of a pipe or pipeline, comprising:

obtaining a probe comprising an optical sensor or viewer comprising a lens capable of viewing about 360 degrees, a direction locator, and a distance measurer, wherein said probe is in communication with a computer or data processor for processing data from said probe;

passing said probe through the interior of said pipeline while illuminating at least a portion of said pipeline interior wall with said light source and viewing and transmitting for recording views of said pipeline interior wall where illuminated with said probe;

recording said location and distance of said probe in said pipeline as data for at least some of said views; and processing said recorded views and direction and distance data such that said views are digitized and displayed in real-time as forward views and side-scan views and wherein said side-scan views are unfolded images showing approximately 360 degrees of the pipeline wall.

2. The method of claim 1 further comprising saving for later analysis said digitized views and data in a data file format suitable for images.

3. The method of claim 1 wherein said location and distance data comprises angle of inclination and axial rotation of probe.

4. A method for detecting defects or damage in the interior wall of a pipe or pipeline, comprising:

providing a probe comprising a light source, an optical sensor or view comprising a lens capable of viewing about 360 degrees, a direction locator comprising a gyro sensor, and a distance measurer, wherein said probe is in communication with a computer or data processor for processing data from said probe;

passing said probe through the interior of said pipeline while illuminating at least a portion of said pipeline interior wall with said light source and viewing and transmitting for recording views of said pipeline interior wall where illuminated with said probe;

recording and direction and distance of said probe in said pipeline as data for at least some of said views as the probe passes through the pipeline;

processing said recorded views and direction and distance data such that said views are digitized and displayed in real-time as forward views and side-scan views, wherein said side-scan views are unfolded images showing approximately 360 degrees of the pipeline wall, and wherein said direction is obtained from pipeline deflection calculated using gyro sensor data by integrating the following formula:

Theta-e(i)-Theta(t)-Theta-error/1 *t where: Theta-error is the difference in angle observed between gyro data measured as the probe goes forward and comes back through the pipeline: T is total time; Theta(t) is the time from the beginning of the measurement: and Theta-c(t) is the compensated angle, and returning said probe through said pipeline after passing through said pipeline, and recording said direction locator data as the probe passes through the pipeline and as the probe is returned through the pipeline.

5. The method of claim 4 wherein said direction data from said gyroscope or gyro sensor is adjusted for noise according to the compensation method.

6. The method of claim 4 wherein said optical viewer is a video camera or a CCD camera.

7. The method of claim 6 wherein said views are transmitted by the probe to said computer as analog data which is converted to digital data by said computer and wherein pixels are manipulated on a frame capture board to obtain real-time digitized forward and side-scans views of the pipeline interior.

8. The method of claim 6 wherein said views comprise digital data that has been compressed and wherein said views are digitally transmitted by the probe to said computer for display and storage.

9. The method of claim 6 where said views comprise digital data whose pixels are manipulated to obtain real time digitized forward and side-scan views of the pipeline interior.

10. An apparatus for detecting defects or damage in the interior of a sewer pipeline comprising a sewer pipeline inspection probe and data processing software that digitizes data from said probe in real time, providing both forward and unfolded side-scan of the sewer pipeline interior, wherein said software includes instructions for manipulating the pixels from the digitized views such that at least one sampling circle is obtained for each frame of the forward view and successive scans can be concatenated so that the side-scan view may be displayed as an unfolded, laid-flat, side-scan image encompassing about 360 degrees.

11. The apparatus of claim 10 wherein said probe comprises a light source for illuminating the pipeline interior and an optical sensor or camera comprising a fish-eye lens for obtaining forward and side-scan views in the pipeline.

12. The method for detecting defects or damage in a pipeline comprising passing the apparatus of claim 10 through said pipeline; taking forward views of the interior wall of said pipeline; digitizing and processing said views; simultaneously displaying digitized forward and side-scan images in real time, wherein said side-scan images are unfolded 360 degree images; and saving said images for further evaluation.

13. A method for obtaining real-time unfolded side-scan images of an interior pipeline wall substantially simultaneously or synchronously with forward images of the pipeline interior for use in inspecting the pipeline wall for defects or damage, said method comprising: passing a lighted probe comprising a camera with a fish-eye lens through said pipeline obtaining forward or frontal views having about a 360 degree radius at periodic intervals; relaying said views in analog data format to a data processor or computer; converting said analog data to digital data; manipulating pixels from said digital data on a frame capture board such that at least one sampling circle is obtained for each side-scan view; displaying an unfolded 360 degree image of the side-scan view of said interior pipeline wall.

14. The method of claim 13 further comprising displaying substantially simultaneously with said side-scan image, a forward or frontal view said interior pipeline wall.

15. The method of claim 13 wherein said side-scan views are recorded about every 0.01 millimeter to about every 100 millimeters along the pipeline interior wall and said forward views are recorded at least about every 10 millimeters to about 1000 millimeters along the pipeline interior wall.

16. The method of claim 15 wherein said pipeline is a sewer line or similar line for transporting liquids or gases or slurries.

17. The method of claim 13 wherein said pipeline is a sewer line and said side-scan views are recorded about every 1 or 2 millimeters along the pipeline interior wall and said forward views are recorded about every 100 millimeters along the pipeline interior wall.

18. The method of claim 13 wherein said side-scan views are recorded more frequently than said forward views but where said side-scan views and said forward views are recorded synchronously.

19. A method for detecting internal pipeline defects or damage, comprising: passing a lighted probe comprising a video camera with a fish-eye type of lens through at least a portion of the interior of said pipeline, illuminating said pipeline and recording forward and side-scan images periodically and synchronously during said passing; noting simultaneously with said recording of at least said side-scan images the location of the probe in the pipeline at the time of recording of said image; and digitizing and processing said images for display wherein said processing comprises pixel manipulation on at least one line of a sampling circle to obtain an unfolded image of the side-scan view.

20. The method of claim 19 wherein said pixel manipulation is done on a frame capture board.

21. The method of claim 19 wherein said display includes both forward views and side-scan.

22. The method of claim 19 further comprising saving said digitized images for later evaluation or use.

23. The method of claim 22 wherein said images are saved in a data file format for images.

* * * * *